(12) United States Patent
Kim et al.

(10) Patent No.: US 8,227,416 B2
(45) Date of Patent: Jul. 24, 2012

(54) METHOD FOR TREATING PAIN INDUCED BY TRAUMATIC PERIPHERAL NERVE INJURY BY ADMINISTRATION OF G-CSF

(75) Inventors: Kyung-Soo Kim, Seoul (KR); Jun-Ho Joe, Paju-si (KR)

(73) Assignee: Industry-University Cooperation Foundation, Hanyang University (KR)

( * ) Notice: Subject to any disclaimer, the term of this patent is extended or adjusted under 35 U.S.C. 154(b) by 47 days.

(21) Appl. No.: 12/935,779

(22) PCT Filed: Mar. 20, 2009

(86) PCT No.: PCT/KR2009/001438
§ 371 (c)(1),
(2), (4) Date: Sep. 30, 2010

(87) PCT Pub. No.: WO2009/116836
PCT Pub. Date: Sep. 24, 2009

(65) Prior Publication Data
US 2011/0020268 A1    Jan. 27, 2011

(30) Foreign Application Priority Data
Mar. 21, 2008  (KR) ................ 10-2008-0026272

(51) Int. Cl.
*A01N 37/18*  (2006.01)
(52) U.S. Cl. ........ 514/18.3; 514/18.2; 514/7.6; 514/9.4; 514/17.7
(58) Field of Classification Search .............. None
See application file for complete search history.

(56) References Cited

U.S. PATENT DOCUMENTS

| 2007/0081970 A1 | 4/2007 | Fukuda et al. |
| 2007/0098680 A1 | 5/2007 | Kawabe et al. |
| 2010/0048869 A1 | 2/2010 | Kim et al. |

OTHER PUBLICATIONS

Hofer et al., 2005, Physiol. Res. 54, pp. 207-213.*
Koda et al. 2007, Brain Res., 1149, pp. 223-231.*
Stratos et al., 2007, J. Appl. Physiol., 103, pp. 1857-1863.*
Meuer et al., 2006, J. Neurochem., 97, pp. 675-686.*
Schneider et al., 2005, J. Clin. Investig., 115(8), pp. 2083-2098.*
Tanaka et al., 2006, J. Neuropathol. Exp. Neurol., 65(8), pp. 816-825.*
W.S. Al-Amood et al., "Effects of Chronic Electrical Stimulation on Contractile properties of Long-Term Denervated Rat Skeletal muscle," Journal of Physiology, vol. 441, 1991, pp. 243-256.
David G. Kline et al., "Operative management of selected brachial plexus lesions," J. Neurosurg, vol. 58, May 1983, pp. 631-649.
David G. Kline, "Civilian gunshots wounds to the brachial plexus," J. Neurosurg, vol. 70, Feb. 1989, pp. 166-174.
Keun-Hwa Jung et al., "Granulocyte colony-stimulating factor stimulates neurogenesis via vascular endothelial growth factor with STAT activation," Brain Research, vol. 1073-1074, 2006, pp. 190-201.

* cited by examiner

*Primary Examiner* — Olga N Chernyshev
(74) *Attorney, Agent, or Firm* — Cantor Colburn LLP

(57) ABSTRACT

Disclosed herein are an agent for treating traumatic peripheral nerve injury comprising a granulocyte colony stimulating factor (G-CSF) as an active ingredient and a method for treating traumatic peripheral nerve injury with the same.
The therapeutic agent advantageously regenerates nerve cells and blood vessels in peripheral nerve tissues and thus rehabilitates the injured nerve tissues to improve nerve conduction velocity, and relieves pain induced by traumatic peripheral nerve injury.

4 Claims, 4 Drawing Sheets
(3 of 4 Drawing Sheet(s) Filed in Color)

(a) Sham group (b) Experimental group (c) Control group

Toluidine blue stained cross section of rat sciatic nerve. (×200)

METHOD FOR TREATING PAIN INDUCED BY TRAUMATIC PERIPHERAL NERVE INJURY BY ADMINISTRATION OF G-CSF

TECHNICAL FIELD

The present invention relates to an agent for treating traumatic peripheral nerve injury comprising a granulocyte colony stimulating factor (G-CSF) as an active ingredient and a method for treating traumatic peripheral nerve injury with the same.

BACKGROUND ART

The nervous system is divided broadly into two categories: the peripheral nervous system and the central nervous system. The peripheral nervous system is composed of sensory neurons and the neurons that connect them to the spinal cord and brain, which make up the central nervous system, and performs nerve conduction.

The peripheral nervous system is divided into the somatic nervous system and the autonomic nervous system, and the somatic nervous system is divided into cranial nerves and spinal nerves. Meanwhile, depending on the function thereof, the somatic nervous system is divided into afferent (or sensory) nerve fibers and efferent (or motor) nerve fibers. The afferent (or sensory) nerve fibers are responsible for transmitting nerve signals derived from sensory receptors to central nerves, and the efferent (or motor) nerve fibers are responsible for performing nerve conduction from the brain and spinal cord to muscles and secretory glands.

Cranial nerves, peripheral nerves emerging from the brain, are organized into twelve pairs which consist of sensory, motor and mixed nerve fibers. The twelve pairs of cranial nerves are olfactory nerves, optic nerves, oculomotor nerves, trochlear nerves, trigeminal nerves, abducens nerves, facial nerves, vestibulocochlear nerves, glossopharyngeal nerves, vagus nerves, accessory nerves and hypoglossal nerves.

Of these, nerves composed of sensory or combined nerve fibers are olfactory nerves, optic nerves, abducens nerves, facial nerves, vestibulocochlear nerves, glossopharyngeal nerves and vagus nerves.

The spinal nerves, peripheral nerves coming out of the spinal cord, are organized into 31 pairs in the left and right sides of the body: 8 cervical, 12 thoracic, 5 lumbar, 5 sacral, and 1 coccygeal. The spinal nerves are all mixed nerve fibers, each of which contains both sensory nerve fibers supplied to the skin, and motor nerves supplied to the muscles.

Sensory nerve fibers, i.e., sensory nerves, accurately serve to transmit stimuli, e.g., light, sound, temperature or touch received by sensory acceptors such as the visual organ, auditory organ, olfactory organ, gustatory organ and the skin, to the central nervous system. Then, the nerve signals are finally transmitted from the central nervous system to the sensory areas, e.g., visual and auditory areas, in the cerebral cortex, to perform normal sensation.

However, these peripheral nerves may be injured by factors such as viral infection, tumors, cancers, ischemia, trauma, compression, pharmacotherapy or actinotherapy. The injury symptoms include peripheral tingling, numbness and burning sensation, decrease in intrinsic and vibration angles of joints, and joint pain, dysesthesia, chills and burning, etc.

These peripheral nerve injuries are generally divided into traumatic peripheral nerve injuries, congenital peripheral nerve injuries, inflammatory peripheral nerve injuries, toxic peripheral nerve injuries, and other tumorous or idiopathic peripheral nerve injuries (Dyck, et al. WB Sounders Co. Philadelphia. *Peripheral Neuropathy,* 1435-1451, (1984); Brown W F. *The place of Electro-myography in the analysis of Traumatic peripheral nerve lesion*. In (1987): Brown W F, Bolton, C F. Clinical Electromyography. Butterworth, 159-175).

Of these, the traumatic peripheral nerve injuries increasingly occur in more various patterns, due to increased industrial mishaps and traffic accidents, and generalized sport and leisure which are caused by the industrial development and rapid automobile popularization.

In the treatment of traumatic peripheral nerve injury caused by physical injury to nerves, symptomatic therapy is currently used for the purpose of symptom relief. For example, there are operations, e.g., removal of the wound site around the injured tissue to promote regeneration of peripheral nerves (Kline D G et al. *Civilian gunshot wound to brachial plexus.* 70, 166-174, (1989)), an operation to directly bind upper and lower portions of the injured site (Kline D G, Judice D J: *Operative management of selected brachial plexus lesions. J Neurosurg* 58, 631-649, (1983)), and peripheral nerve grafting (Millesi H; *Brachial plexus injuries. Nerve grafting. Clin Orthop* 237, 36-42. (1988)).

Meanwhile, there are several conservative therapies, e.g., electrotherapy to prevent the degeneration of neuromuscular junctions and muscular atrophy, while awaiting voluntary nerve regeneration (al-Amood W S, Lewis D M, Schmalbruch H, *Effects of chronic electrical stimulation on contractile properties of long-term denervated rat skeletal muscle. J Physiol (London)* 441, 243-256, (1991), and exercise therapy generally-used in partial injuries, to prevent weakness and atrophy of muscular strength and promote collateral sprouting of nerves. Another conservative therapy is the use of an orthotic to protect the joint and prevent muscle and ligament injury (Gravois M, Garrison S J, Hart K A, Lehmkuhl L D: *Physical Medicine and Rehabilitation*, Massachusetts: Blackwell Science, 432-433, (2000)). Furthermore, there is a drug therapy to relieve the pain caused by nerve injury using local anesthetics and antispasmodics.

However, the operative therapies may induce secondary injury, and clinically useful drugs which directly act on the injured peripheral nerve system to fundamentally treat the injury are hardly known in the field of drug therapy.

Meanwhile, the granulocyte-colony stimulating factor (G-CSF) specifically acts on neutrophil stem cells to promote the proliferation and differentiation of neutrophils and increase antibody-dependent cell-mediated cytotoxicity. In addition, G-CSF promotes IgA-mediated phagocytosis and increases superoxide production performance. Accordingly, G-CSF is known to improve reactivity to chemotactic peptides, inhibits occurrence of infectious diseases, and reduces the frequency of pyrexia.

In addition, G-CSF is believed to have little effect upon leukemic stem cells in the body, since it acts on more differentiated bone marrow cells, as compared to other CSFs such as granulocyte-macrophage CSFs (GM-CSFs). Accordingly, G-CSF is widely used for anti-cancer chemotherapy, administration of a great amount of anti-cancer agent, combination therapy with radiotherapy, and a drug for promoting rehabilitation of neutrophils after bone narrow implantation (Julie M. Vores et al., *Clinical Applications of Hematopoietic Growth Factors, Journal of Clinical Oncology,* 13, 1023-1035, (1995)).

Such G-CSF acts as a hematopoietic agent that primarily acts on the proliferation and differentiation of neutrophils, which is primarily used for the treatment of neutropenia caused by bone marrow transplantation and anti-cancer administration and is responsible for increasing neutrophils in myelodysplastic syndromes, aplastic anemia, serious chronic neutropenia (such as congenital, cyclic or idiopathic neutropenia), HIV-infected patients and preventing infectious diseases caused by decreased neutrophils.

In recent years, a great deal of research has been conducted on, in addition to clinical use of G-CSF for the neutropenia, on administration of G-CSF alone or in combination with an antibiotic for the treatment of infectious diseases, based on the expectation that G-CSF promotes neutrophil production and reinforces neutrophil performance, thus being potent for preventing and treating various infectious diseases such as pneumonia or septicemia.

Several therapeutic agents using G-CSF, based on various physiological activities, were suggested. For example, Korean Patent Application No. 10-2005-7019543 discloses a diabetes treatment comprising one or more stem cell-recruiting factors such as G-CSFs as active ingredients. In addition, Korean Patent Application No. 10-2006-7008042 discloses a fibroblast-mobilizing agent using G-CSF to simply recruit fibroblasts into wounded tissues and engraft the fibroblasts in the wounded tissues, thereby healing the wounds.

However, there is no research that recognizes the treatment of traumatic peripheral nerve injuries as a novel use of G-CSF.

DISCLOSURE

Technical Problem

Therefore, the present invention has been made in view of the above problems, and it is an object of the present invention to provide an agent for treating traumatic peripheral nerve injury comprising a granulocyte colony stimulating factor (G-CSF) as an active ingredient and a method for treating traumatic peripheral nerve injury with the same.

Technical Solution

In accordance with one aspect of the present invention, the above and other objects can be accomplished by the provision of an agent for treating traumatic peripheral nerve injury comprising a granulocyte colony stimulating factor (G-CSF) as an active ingredient and a method for treating traumatic peripheral nerve injury with the same.

Advantageous Effects

The therapeutic agent of the present invention advantageously regenerates blood vessels in the injured peripheral nerve tissues and rehabilitates the injured nerve tissues, thereby improving nerve conduction velocity and relieving the pain of nerve injury.

DESCRIPTION OF DRAWINGS

The patent or application file contains at least one drawing executed in color. Copies of this patent or patent application publication with color drawings will be provided by the office upon request and payment of the necessary fee.

The above and other objects, features and other advantages of the present invention will be more clearly understood from the following detailed description taken in conjunction with the accompanying drawings, in which.

Best Mode

Figure 1:
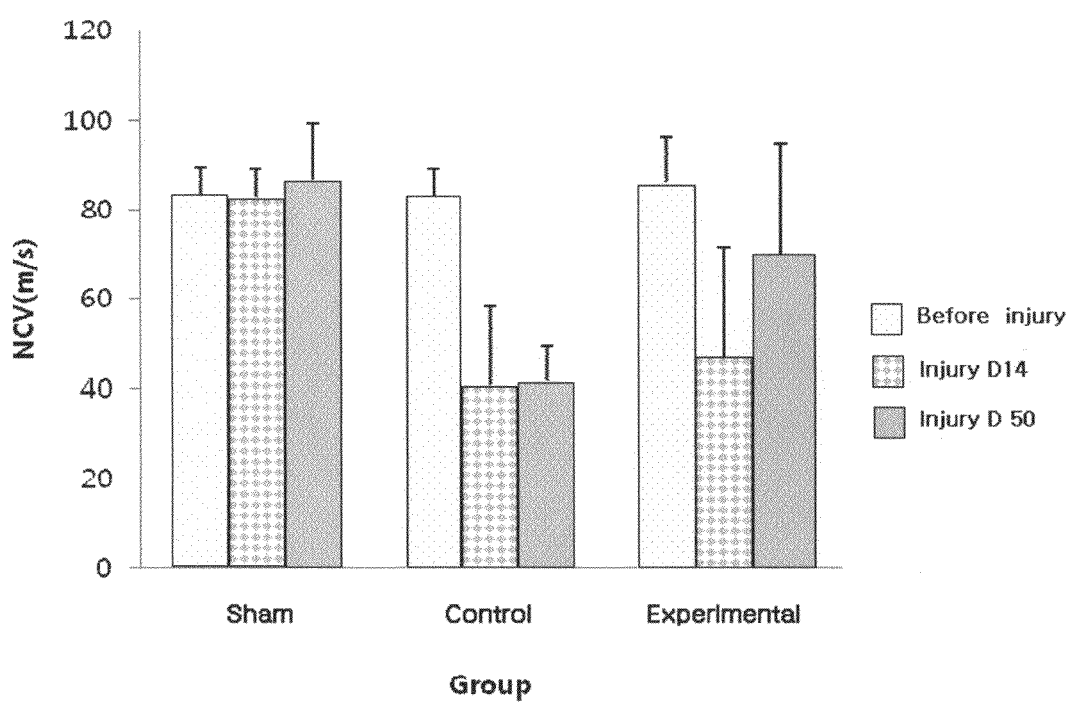
FIG. 1 is a graph showing nerve conduction velocity measured before nerve injury, after nerve injury and on $14^{th}$ and $50^{th}$ days after nerve injury, for a sham group, an experimental group and a control group.

The term "traumatic peripheral nerve injury"? used throughout the disclosure refers to a physically injured peripheral nerve, which includes all injuries due to traffic accidents, injuries by glasses or knives, falls, traumatic injuries directly caused by iron or wood, gunshot wounds, injuries by machinery, injuries by exercise, compression, electrical burn, explosions, injuries by fracture and dislocation, and injuries by operations.

Hereinafter, the present invention will be illustrated in more detail.

During research on various physiological activities of granulocyte colony stimulating factor (hereinafter, referred to as 'G-CSF'), the inventors of the present invention discovered that G-CSF regenerates blood vessels in peripheral nerve tissues and rehabilitates the injured nerve tissues, thus improving nerve conduction velocity and pain sensitivity, thereby being useful as a preventive and therapeutic agent for diabetic peripheral neuropathies. Korean Patent No. 0812274 was granted to the present inventors, based on the discovery.

In the process of a great deal of research to confirm whether G-CSF is efficacious for novel indications, in addition to diabetic peripheral neuropathies, the present inventors identified that G-CSF relieves pain induced by traumatic peripheral nerve injury and induces regeneration of nerve cells in the nerve tissues, and is thus useful as a therapeutic agent for traumatic peripheral nerve injuries. Based on such identification, the present invention has been completed.

The therapeutic agent of the present invention contains G-CSF as an active ingredient. In addition, the method for treating traumatic peripheral nerve injuries according to the present invention comprises administering a therapeutically effective amount of G-CSF to a subject in need thereof.

Any G-CSF may be used without particular limitation so long as it exhibits biological activity substantially identical to human G-CSF. Representative examples of useful G-CSF include natural G-CSF and recombinant G-CSF. Preferred is the use of those having the same amino acid sequence as natural G-CSF. Most preferred is the use of recombinant human granulocyte colony stimulating factor (rhG-CSF).

The origin of G-CSF is not particularly limited in the present invention. The G-CSF may be prepared by separating from a mammal, synthesizing chemically, or genetically expressing an exogenous DNA sequence obtained by genome or cDNA cloning or DNA synthesis in a prokaryotic or eukaryotic host cell. The prokaryotic host useful for the genetic expression includes various bacteria (e.g., *E. coli*) and suitable eukaryotic hosts include yeast (e.g., *S. Serevisiae*) and mammalian cells (e.g., Chinese hamster ovary cells or monkey cells).

The G-CSF obtained by gene recombination includes G-CSF having the same amino acid sequences as natural G-CSF, or G-CSF having an amino acid sequence wherein one or more amino acid is deleted, substituted, or added.

These G-CSFs and analogs thereof may be used by obtaining from a variety of suppliers and purifying the same.

The traumatically injured peripheral nerve is selected from the group consisting of ulnar nerve, median nerve, brachial plexus, radius nerve, peroneal nerve, sciatic nerve, tibial nerve and a combination thereof. As can be seen from Experimental Example 2, the experimental group, wherein the therapeutic agent of the present invention is administered to SD rats with traumatically-injured sciatic nerves, exhibited increased reduced nerve conduction velocity due to nerve injury, as compared to the control group (See FIG. 1).

Figure 2:
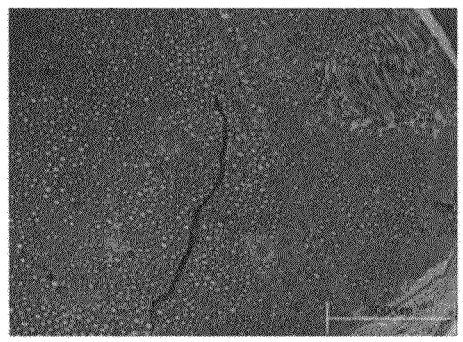
FIG. 2(a) is an image showing toluidine blue-stained sciatic nerve tissues of the sham group.
FIG. 2(b) is an image showing toluidine blue-stained sciatic nerve tissues of the experimental group.
FIG. 2(c) is an image showing toluidine blue-stained sciatic nerve tissues of the control group.
Figure 2:
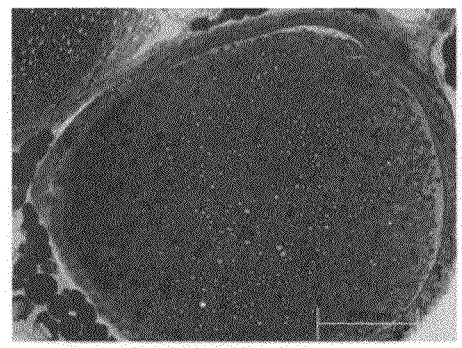
Figure 2:
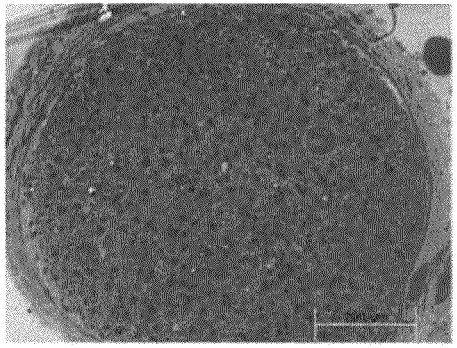

In addition, as can be seen from Experimental Example 3, the experimental group, wherein the therapeutic agent of the present invention is administered to SD rats with traumatically-injured sciatic nerves, had a great deal of normal tissues similar to the sham group, which indicates that nerve tissues were regenerated (See FIG. 2).

Figure 3:
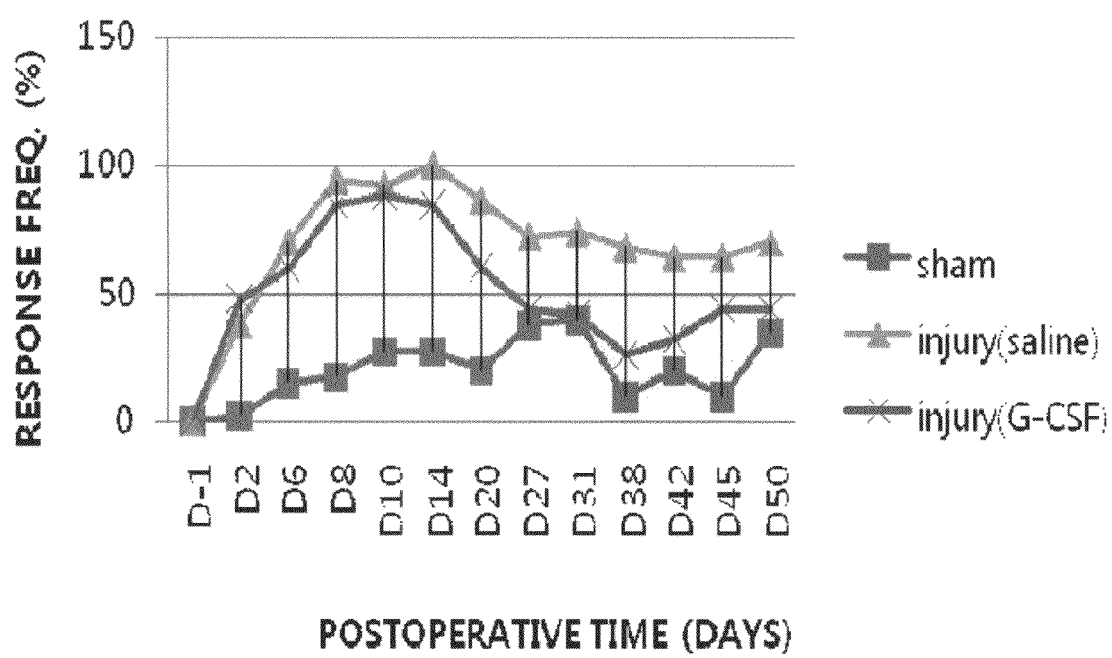
FIG. 3 is a graph showing avoidance frequency to cold allodynia for the sham group, the control group and the experimental group.
Figure 4:
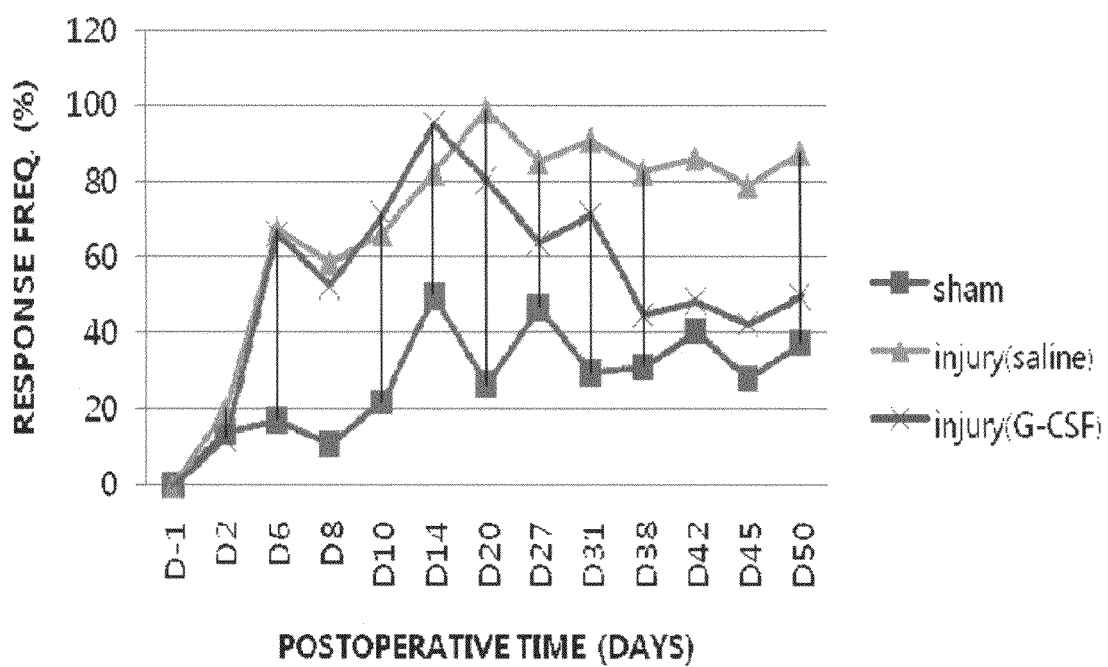
FIG. 4 is a graph showing avoidance frequency to mechanical allodynia for the sham group, the control group and the experimental group.

In addition, as can be seen from Experimental Examples 4 and 5, when the therapeutic agent of the present invention is administered to SD rats with traumatically-injured sciatic nerves, exhibited decreased pain to cold and mechanical allodynia owing to the administration of G-CSF (See FIGS. 3 and 4).

These behaviors occur because G-CSF releases functional stem cells in the bone narrow to peripheral blood and induces differentiation of the released cells, thereby regenerating nerve cells and blood vessels in the peripheral nerve tissues, restoring the injured nerve tissues, promoting blood supply to nerves and regenerating peripheral nerves. In addition, the G-CSF exhibits relief activity to the pain induced by traumatic peripheral nerve injury.

The therapeutic agent of the present invention comprising G-CSF as an active ingredient may contain the active ingredient in an amount of 0.0001 to 50% by weight, based on the total weight of the therapeutic agent composition.

In addition, the therapeutic agent of the present invention, in addition to the active ingredient, may further comprise one or more active ingredients exhibiting the same or similar functions to the active ingredient.

The therapeutic agent of the present invention comprising G-CSF as an active ingredient may further comprise at least one pharmaceutically acceptable carrier in addition to the above-mentioned active ingredient to preferably prepare a pharmaceutical composition. In preparing the composition in a liquid solution, as the pharmaceutically acceptable carrier, which is suitable for sterilization and in vivo, may be selected from the group consisting of saline, sterilized water, Ringer's solution, buffered saline, an albumin injection solution, a dextrose solution, a maltodextrin solution, glycerol, ethanol, or a mixture thereof. If necessary, the composition may further comprise other typical additives such as an antioxidant, a buffer, or a bacteriostatic agent. Further, the composition may be prepared into a form of injections such as a solution, a suspension or an emulsion, pills, capsules, granules or tablets, by adding a diluent, a dispersant, a surfactant, a binder, or a lubricant thereto. The composition may be used by bonding an antibody specific for a target organ or other ligands to the carrier such that the composition has a function specific for the target organ.

A pharmaceutical form of the therapeutic agent of the present invention comprising the G-CSF as an active ingredient may be granules, powders, coated tablets, capsules, suppositories, syrups, juices, suspensions, emulsions, drops, injectable solutions, and also preparations enabling sustained release of active compounds.

The therapeutic agent of the present invention comprising the G-CSF as an active ingredient may be administered in a typical method through an intravenous, intra-arterial, intraperitoneal, intrasternal, intradermal, nasal, inhalant, topical, rectal, oral, intraocular or subcutaneous route. The administration method is not particularly limited, but a non-oral administration is preferable, and the subcutaneous administration is more preferable.

Dosages of the therapeutic agent of the present invention may be adjusted depending on various factors such as a type of homoiothermal animal comprising human in need of administration, a type of disease, a degree of illness, a type and content of an active ingredient and other components contained in a composition, a type of pharmaceutical form, a patient's age, weight, general health status, gender and diet, an administration time, an administration route, a flow rate of a composition, a treatment duration, and other drugs used simultaneously. In case of an adult, when the G-CSF is administered once daily at a dose of 0.01 µg/kg/day to 100 µg/kg/day, and preferably 0.01 µg/kg/day to 10 µg/kg/day. The administration may be performed once daily or divisionally several times.

The therapeutic agent of the present invention may be used alone or in combination with other methods such as surgical operations.

The therapeutic agent of the present invention regenerates nerve cells and blood vessels in peripheral nerve tissues to rehabilitate injured nerve tissues and thus improves nerve conduction velocity and relieves pain due to peripheral nerve injury. Accordingly, the therapeutic agent of the present invention is useful for the treatment of traumatic peripheral nerve injury.

Mode for Invention

Hereinafter, examples will be provided for a further understanding of the invention. The following examples are for illustrative purposes only and are not intended to limit the scope of the present invention.

EXPERIMENTAL EXAMPLE 1

Therapeutic Activity of G-CSF on Traumatic Peripheral Nerve Injury

Animals used herein were ~300 g adult Sprague-Dawley (SD) rats which had been acclimated to the laboratory surroundings for 5 days, while being sufficiently fed with a solid feed (Samyang Co., Ltd., for cattle animal application) and water. The lab temperature was maintained in the range of 24 to 26° C. and the animals were slept at 12 h/12 h cycles.

The test groups were divided into three groups, i.e., a sham group (normal group) whose nerve was not injured after operation, an experimental group wherein nerves were injured and G-CSF was administered after operation, and a control group wherein nerves were injured and saline was administered after operation. For the number of respective groups, the sham group (normal group) is 8, the experimental group is 10 and the control group 10, for a total of 28.

Nerve injury models were established by compressing sciatic nerves with forceps.

Specifically, SD rats were anesthetized by injecting 50 mg/kg of ketamine and 9.6 mg/kg of xylazine into the abdomen thereof, were depilated on the gluteal and femoral regions of both lower limbs, and were then placed in the prone position. The femoral region was sterilized with potadine and 70% alcohol, 2 cm of epidermal cells based on the center thereof was longitudinally incised to turn over the musculus biceps femoris and to thus expose the sciatic nerve. The nerve injury is made by incising 2 cm of epidermal cells interposed between the greater trochanter and the knee joint, stripping gluteal muscles and the knee joint muscles to expose sciatic nerves and applying crushing injury on the region where nerves appear at the sciatic notch with the forceps for 30 seconds. The nerve was injured by marking a black line within 5 mm adjacent to the end of the forceps and compressing nerves in the constant region, such that a constant strength is applied to a predetermined region. The sham group (normal group) was subjected to operation in the same manner as in the experimental and control groups except that its nerves were injured with forceps. After operation, the wound was sealed and sterilized.

14 days after operation (injury D14), G-CSF (Leucostim available from Dong-a pharm. Co., Ltd.) was administered once daily at 100 μg/kg/day for 5 days to the abdominal subcutis of the experimental group, and 0.2 ml of saline was intraperitoneally administered once daily for 5 days to the control group and the sham group (normal group). Then, the test groups were observed for about 4 weeks.

EXPERIMENTAL EXAMPLE 2

Nerve Conduction Test

The nerve conduction test was performed after SD rats were anesthetized with a mixed solution of ketamine and xylazine. The sciatic notch was selected as the stimulated site, an active-recording electrode was placed on the leg muscles, a counter electrode was placed on the foot, and a ground electrode was placed between a stimulating electrode and a recording electrode. An adhesive electrode was used as the recording electrode and a pin electrode as the ground electrode was placed on the subcutis.

The nerve conduction test was performed with KeyPoint (Dantec, Denmark). The frequency, sweep velocity, and sensitivity were 2 to 10,000 Hz, 2 msec/division, and 5 mV/division, respectively. The nerve conduction test was performed before operation, on the $14^{th}$ day after the operation (injury D14) and on the $50^{th}$ day after the operation (injury D50). For the test, the latency and width were determined by measuring onset latency, and the width from a base line to a cathode peak, respectively.

The nerve conduction test was carried out by obtaining three respective values from the both sides, for the sham group (normal group, n=8), the experimental group (n=10) and the control group (n=10). The laboratory temperature was maintained at 25° C. or higher and the skin temperature of SD rats was maintained at 30° C. or higher. The results thus obtained are shown in Table 1 below and FIG. 1.

TABLE 1

| | [Nerve conduction velocity (m/s)] | | |
| --- | --- | --- | --- |
| Test Groups | Before operation | D 14 | D 50 |
| Sham group | 83.4 | 82.1 | 86.9 |
| Control group (saline-administration) | 82.8 | 39.2 | 40.8 |
| Experimental Group (G-CSF administration) | 85.8 | 47.8 | 69.7 |

As can be seen from FIG. 1, the experimental group and the control group showed decreased nerve conduction velocity due to nerve injury. On the other hand, the G-CSF-administered experimental group increased in nerve conduction velocity, as compared to the control group, and the saline-administration group.

EXPERIMENTAL EXAMPLE 3

Histopathological Examination

On the $50^{th}$ day after operation (injury D 50), sciatic nerve tissues of each group were extracted in order to identify the tissue variation and neurohistological examination was performed using toluidine blue staining. The results thus obtained are shown in FIG. 2.

As can be seen from FIG. 2, as compared to the control group (saline-administered group), the experimental group (G-CSF-administered group) had a great deal of normal tissues similar to the sham group, which indicates that nerve tissues were regenerated.

EXPERIMENTAL EXAMPLE 4

Behavior Test to Cold Allodynia

Whether or not cold allodynia was observed on 1, 2, 6, 8, 10, 14, 20, 27, 31, 38, 42, 45 and $50^{th}$ days after operation, was confirmed.

Specifically, pain in response to cold stimuli was measured by dropping acetone on the plantar of the injured leg to perform avoidance response (Tal et al., Onset of ectopic firing in the Chung model of neuropathic pain coincides with the onset of tactile allodynia, Proceedings of the 11th World Congress on Pain). The acetone was dropped on the plantar of the injured leg five times at five-minute intervals using a polyethylene tube connected to a syringe. The response frequency (%) was determined by dividing the leg avoidance frequency by the total number of tests and calculating as a percentage. The results thus obtained are shown in FIG. 3.

As can be seen from FIG. 3, the normal group (sham group) was not injured by operation, but felt pain by the operation. As compared to the control group (saline-administered group), the experimental group (G-CSF-administered group) exhibited decreased avoidance frequency to cold allodynia, which indicates that pain induced by nerve injury was relieved.

EXPERIMENTAL EXAMPLE 5

Behavior Test to Mechanical Allodynia

Whether or not mechanical allodynia was observed on 1, 2, 6, 8, 10, 14, 20, 27, 31, 38, 42, 45 and $50^{th}$ days after operation, was confirmed. Specifically, harmless mechanical stimuli not normally inducing pain were applied to the plantar of the injured leg using von Frey hair (15 gm; 147 mN). The plantar was slightly stimulated with the von Frey hair, to find and mark the site sensitive to the mechanical stimuli. The leg skin was stimulated ten times at 10-20-minute intervals on the marked point. As the response frequency increases, the pain response increases. 0.5 cm or higher of rough sudden avoidance response was counted as a frequency. The response frequency (%) was represented by the frequency of avoidance responses/10(trial frequency)×100, and the results thus obtained are shown in FIG. 4.

As can be seen from FIG. 4, the normal group (sham group) was not injured by operation, but felt pain by the operation. As compared to the control group (saline-administered group), the experimental group (G-CSF-administered group) exhibited decreased avoidance frequency to mechanical allodynia, which indicates that the pain induced by nerve injury was relieved.

Industrial Applicability

As apparent from the foregoing, the therapeutic agent of the present invention is useful for the treatment of traumatic peripheral nerve injury.

The invention claimed is:

1. A method of treating pain induced by traumatic peripheral nerve injury, comprising administering a therapeutically effective amount of granulocyte-colony stimulating factor (G-CSF) to a patient in need thereof.

2. The method according to claim 1, wherein the G-CSF is obtained and separated from natural origin.

3. The method according to claim 1, wherein the G-CSF is a recombinant human granulocyte colony stimulating factor (rhG-CSF).

4. The method according to claim 1, wherein the peripheral nerve is selected from the group consisting of ulnar nerve, median nerve, brachial plexus, radius nerve, peroneal nerve, sciatic nerve, tibial nerve and a combination thereof.

* * * * *